United States Patent [19]

Vallejos et al.

[11] Patent Number: 5,306,833
[45] Date of Patent: Apr. 26, 1994

[54] PREPARATION PROCESS FOR ARYLACETIC ACIDS AND THEIR ALKALI METAL SALTS

[75] Inventors: Jean-Claude Vallejos; Yani Christidis, both of Paris, France

[73] Assignee: Societe Francaise Hoechst, Puteaux, France

[21] Appl. No.: 12,632

[22] Filed: Feb. 3, 1993

[30] Foreign Application Priority Data

Feb. 4, 1992 [FR] France .................... 92 01215

[51] Int. Cl.$^5$ .............. C07C 51/377; C07C 67/297; C07D 333/24
[52] U.S. Cl. ........................ 549/79; 549/447; 560/55; 560/56; 560/76; 560/100; 560/105; 562/465; 562/466; 562/478; 562/490; 562/496
[58] Field of Search ............. 549/79, 447; 560/55, 560/100, 56, 76, 105; 562/465, 478, 490, 496

[56] References Cited

U.S. PATENT DOCUMENTS

| | | | |
|---|---|---|---|
| 4,266,067 | 5/1981 | Fujisawa et al. | 549/79 |
| 4,339,594 | 7/1982 | Spielmann et al. | 562/465 |

FOREIGN PATENT DOCUMENTS

| | | |
|---|---|---|
| 2715785 | 10/1977 | European Pat. Off. |
| 0028375 | 10/1980 | European Pat. Off. |
| 0221815 | 10/1986 | European Pat. Off. |
| 1575808 | 10/1980 | United Kingdom |

OTHER PUBLICATIONS

M. Hudlicky "Reductions in orgainc chemistry" (1984) Ellis Horwood Ltd., Chichester, GB pp. 13, 36.
Houben-Weyl methoden der Organischen Chemie, edition 4, tome IV/1c; Rduktion, partie 1, pp. 67–76; (1980) Georg Thieme Verlag, Stuttgart, De, pp. 67–70, 73.

*Primary Examiner*—Richard L. Raymond
*Attorney, Agent, or Firm*—Browdy and Neimark

[57] ABSTRACT

Process for obtaining an arylacetic acid of general formula (I):

$$Ar-CHR-COOH \qquad (I)$$

in which R=H, $C_1$–$C_4$ alk, Ar=2-thienyl, 3-thienyl, 1-naphthyl, 2-naphthyl, 1-(2-methoxy naphthyl), 3,4-methylenedioxy phenyl or phenyl of general formula (II):

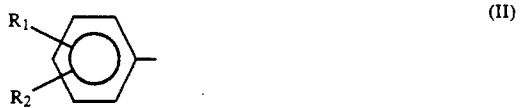

in which $R_1$=H, OH or $C_1$–$C_4$ alkoxy, $R_2$=H, $C_1$–$C_4$ alk, $C_1$–$C_4$ alkoxy or OH, as well as their alkali metal salts, by reaction in a solvent of the corresponding arylglycolic acid of general formula (III):

$$Ar-CR(OH)-COOH \qquad (III)$$

or one of its alkali metal salts with a hydrogen donor agent chosen from the group constituted by: formic acid, or one of its alkali metal salts, phosphonic acid, phosphinic acid, or one of their alkali metal salts, in the presence of a hydrogen transfer catalyst, which if desired is isolated or salified, and use for the preparation of certain acids of formula (I).

20 Claims, No Drawings

PREPARATION PROCESS FOR ARYLACETIC ACIDS AND THEIR ALKALI METAL SALTS

The present invention relates to a preparation process for arylacetic acids and their alkali metal salts.

The arylacetic acids accessible by the process of the present invention are acids of general formula (I):

Ar—CHR—COOH     (I)

in which R represents a hydrogen atom or a $C_1$-$C_4$ alkyl radical and Ar represents an aromatic type radical chosen from the following radicals 2-thienyl, 3-thienyl, 1-naphthyl, 2-naphthyl, 1-(2-methoxy naphthyl), 3,4-methylenedioxy phenyl, the phenyls of general formula (II):

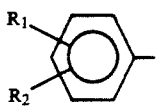

in which $R_1$ represents a hydrogen atom or a hydroxyl or a $C_1$-$C_4$ alkoxyl radical and $R_2$ represents a hydrogen atom or a $C_1$-$C_4$ alkyl radical, a $C_1$-$C_4$ alkoxyl radical or a hydroxyl radical, as well as their alkali metal salts.

The term $C_1$-$C_4$ alkyl can designate, for example, a methyl, ethyl, propyl, butyl, isopropyl, isobutyl, sec-butyl or tert-butyl radical.

The term $C_1$-$C_4$ alkoxyl can designate, for example, a methoxyl, ethoxyl, propoxyl, butoxyl, isopropoxyl, isobutoxyl, sec-butoxyl or tert-butoxyl radical.

The arylacetic acids of general formula (I) and their alkali metal salts are extensively described in the literature, and they are raw materials useful for accessing certain substances having a therapeutic activity, for example an anti-inflammatory activity. It is therefore very useful to be able to prepare them in as rational a manner as possible. It is in particular known that arylacetic acids of general formula (I) can be accessed by either chemical or catalytic hydrogenolysis of the corresponding arylglycolic acids of general formula (III):

Ar—CR(OH)—COOH     (III)

in which Ar and R keep the meaning given previously (cf European Patent Applications No's 3825, 28375, 32374, 124407, 221815, 224401, 265793). However these processes require either raw materials which are rarely available on the market, or costly reagents.

Now the Applicant has discovered with astonishment that it is possible to economically obtain, with good yields, an arylacetic acid of general formula (I) or its alkali metal salt by reacting, in a suitable solvent, the corresponding arylglycolic acid of general formula (III) or one of its alkali metal salts, with a suitable hydrogen donor agent in the presence of a hydrogen transfer catalyst.

The term alkali metal can designate, for example and preferably, sodium or potassium.

The solvents which can be used are, for example, water, acetic acid, water-acetic acid mixtures in variable proportions, diluted aqueous solutions of sodium hydroxide or potassium hydroxide.

The suitable hydrogen donor agents are, for example, formic acid, or one of its alkali metal salts, phosphonic acid, phosphinic acid, or one of their alkali metal salts.

The hydrogen transfer catalysts are, for example, palladium, platinum, rhodium, optionally deposited on an amorphous solid support such as charcoal, calcium carbonate, barium sulphate. Preferably, the hydrogen transfer catalyst is palladium notably deposited on charcoal.

The process according to the present invention is advantageously implemented in water or in a water-acetic acid mixture. The reaction is preferably conducted at atmospheric pressure, at a temperature greater than 50° C., preferably greater than or equal to 80° C., in the presence of an excess of a hydrogen donor agent relative to the stoichiometry, preferably with a 10 to 50% molar excess.

At the end of the reaction, the sought arylacetic acid of general formula (I) is very easily isolated from the reaction mixture by known means. Advantageously, after cooling down to ambient temperature, the reaction mixture is filtered to recover the catalyst, then the filtrate is concentrated under reduced pressure to eliminate the solvents, and the residual oil is dissolved in water at a pH of greater than 7 in the presence of an alkaline mineral agent such as sodium hydrogenocarbonate or sodium hydroxide. The aqueous solution, then acidified to pH=1 with concentrated hydrochloric acid, allows the deposition, generally in the crystallized state, of the sought arylacetic acid which can be, is necessary, purified subsequently according to known means, such as hot and cold recrystallization from an appropriate solvent.

If desired, the acid can be salified into the desired alkali metal salt according to the usual methods, for example by the action of the corresponding alkali metal hydroxide.

The process of the present invention described above is advantageously carried out by dissolving one mole of the chosen arylglycolic acid sodium salt of general formula (III) in a water-acetic acid mixture, then introducing into this solution in succession palladium black with 4±1% palladium, then an excess of the chosen hydrogen donor agent, heating the reaction medium to a temperature greater than 80° C., until the starting product is completely converted, which is followed by chromatographic analysis of a sample taken regularly from the reaction medium, then eliminating the catalyst by filtration and the reaction solvents by distillation under reduced pressure, dissolving the residual oil in water at a pH of greater than 7, and finally, precipitating the desired acid from this aqueous solution by acidification at pH=1.

According to a variant of the process according to the present invention, the operation is carried out in the presence of catalytic quantities of chloride ions. Advantageously, these chloride ions are added by dissolving sodium chloride in the reaction medium. According to an advantageous method, the process of the present invention is carried out in the presence of 0.1 to 0.01 mole of sodium chloride per mole of arylglycolic acid of general formula (III) used.

Among the arylacetic acids of general formula (I) accessible by the process of the present invention, there can be mentioned:
parahydroxyphenylacetic acid
orthohydroxyphenylacetic acid
paramethoxyphenylacetic acid 2-parahydroxyphenyl propanoic acid.

This is why a subject of the present Application is also the use of the process described above for obtaining the arylacetic acids of formula (I) previously mentioned.

The following examples illustrate the present invention.

EXAMPLE 1

A mixture of 52 g (250 mmoles) of sodium parahydroxymandelate crystallized with one molecule of water, 80 g of acetic acid, 25 g of water, 12.9 g (280 mmoles) of formic acid, 9 g (154 mmoles) of sodium chloride and 1.56 g of palladium black with 5% by weight of palladium is heated to boiling point for 10 hours under agitation. The suspension, cooled down to ambient temperature, is then filtered, then the colourless filtrate is concentrated under reduced pressure. The residual oil is dissolved in an aqueous solution of sodium hydrogenocarbonate, then the solution obtained is acidified to pH=1 with concentrated hydrochloric acid. The desired acid crystallizes spontaneously, it is filtered off, then washed with water and dried to a constant weight under reduced pressure at 60° C. In this way 35.75 g (235 mmoles) of pure crystallized parahydroxyphenylacetic acid is obtained, having a melting point of 148°±2° C. (reference literature M.p.=149°–151° C., Beil., 10, 190). The yield is 94% of the calculated theoretical amount relative to the starting acid.

EXAMPLE 2

A mixture of 25.5 g (125 mmoles) of sodium paramethoxymandelate, 80 g of acetic acid, 12.8 g (156 mmoles) of phosphonic acid, 500 mg of sodium chloride and 255 mg of palladium black with 5% by weight of palladium is heated to boiling point for 8 hours under agitation. The analysis of a sample using high pressure liquid chromatography no longer reveals any starting product at this stage of the reaction.

The suspension, cooled down to ambient temperature, is then filtered, then the colourless filtrate is concentrated under reduced pressure. The residual oil is taken up in an aqueous solution of sodium hydrogenocarbonate then the solution obtained is acidified to pH=1 with concentrated hydrochloric acid. The desired paramethoxyphenylacetic acid crystallizes spontaneously, it is filtered off, then it is washed with water by impasting, and finally it is dried to a constant weight under reduced pressure at 60° C. In this way 20 g (120 mmoles) of pure crystallized paramethoxyphenylacetic acid is isolated having a melting point of 84°–85° C.

EXAMPLE 3

Starting with sodium orthohydroxymandelate, orthohydroxyphenylacetic acid was prepared in the same way as that described in Examples 1 and 2.

We claim:

1. Process for obtaining an arylacetic acid of general formula (I):

$$Ar-CHR-COOH \qquad (I)$$

in which R represents a hydrogen atom or a $C_1$-$C_4$ alkyl radical and Ar represents an aromatic type radical selected from the group consisting of 2-thienyl, 3-thienyl, 1-naphthyl, 2-naphthyl, 1-(2-methoxy naphthyl), 3,4-methylenedioxy phenyl and the phenyls of general formula (II):

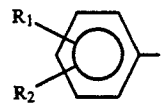

in which $R_1$ represents a hydrogen atom or a hydroxyl or a $C_1$-$C_4$ alkoxyl radical and $R_2$ represents a hydrogen atom or a $C_1$-$C_4$ alkyl radical, a $C_1$-$C_4$ alkoxyl radical or a hydroxyl radical, as well as their alkali metal salts, characterized in that the corresponding arylglycolic acid of general formula (III) or one of its alkali metal salts:

$$Ar-CR(OH)-COOH \qquad (III)$$

is reacted in a solvent with a hydrogen donor agent chosen from formic acid, or one of its alkali metal salts, phosphonic acid, phosphinic acid or one of their alkali metal salts, in the presence of a hydrogen transfer catalyst, which is isolated or, if desired, salified, said catalyst being metallic.

2. Process according to claim 1, characterized in that the solvent used is a mixture of water and acetic acid.

3. Process according to claim 1, characterized in that the solvent used is water.

4. Process according to claim 1, characterized in that the hydrogen transfer catalyst is palladium.

5. Process according to claim 1, characterized in that the hydrogen donor agent is formic acid or one of its alkali metal salts.

6. Process according to claim 1, characterized in that the hydrogen donor agent is phosphonic acid or one of its alkali metal salts.

7. Process according to claim 1, characterized in that the hydrogen donor agent is phosphinic acid or one of its alkali metal salts.

8. Process according to claim 1, characterized in that it is carried out in the presence of catalytic quantities of chloride ions.

9. Process according to claim 8, characterized in that it is carried out in the presence of 0.1 to 0.01 mole of sodium chloride per mole of arylglycolic acid used.

10. Process according to claim 1 wherein parahydroxyphenylacetic acid or one of its alkali metal salts is obtained.

11. Process according to claim 1 wherein paramethoxyphenylacetic acid or one of its alkali metal salts is obtained.

12. Process according to claim 1 wherein orthohydroxyphenylacetic acid or one of its alkali metal salts is obtained.

13. Process according to claim 2, characterized in that the hydrogen transfer catalyst is palladium.

14. Process according to claim 3, characterized in that the hydrogen transfer catalyst is palladium.

15. Process according to claim 2, wherein the hydrogen donor is formic acid or one of its alkali metal salts, phosphonic acid or one of its alkali metal salts or phosphinic acid or one of its alkali metal salts, and wherein said reaction is carried out in a solvent of water, acetic acid, a mixture of water and acetic acid, an aqueous solution of sodium hydroxide, or an aqueous solution of potassium hydroxide.

16. Process according to claim 3, wherein the hydrogen donor is formic acid or one of its alkali metal salts, phosphonic acid or one of its alkali metal salts or phosphinic acid or one of its alkali metal salts.

17. Process according to claim 4, wherein the hydrogen donor is formic acid or one of its alkali metal salts, phosphonic acid or one of its alkali metal salts or phosphinic acid or one of its alkali metal salts.

18. Process according to claim 13, wherein the hydrogen donor is formic acid or one of its alkali metal salts, phosphonic acid or one of its alkali metal salts or phosphinic acid or one of its alkali metal salts.

19. Process according to claim 18, characterized in that it is carried out in the presence of catalytic quantities of chloride ions.

20. Process according to claim 19, characterized in that it is carried out in the presence of 0.1 to 0.01 mole of sodium chloride per mole of arylglycolic acid used.

* * * * *